United States Patent [19]

Gunji et al.

[11] Patent Number: 5,237,599

[45] Date of Patent: Aug. 17, 1993

[54] X-RAY APPARATUS

[75] Inventors: Teruomi Gunji, Otawara; Kazunori Itou, Hadano, both of Japan

[73] Assignee: Kabushiki Kaisha Toshiba, Kawasaki, Japan

[21] Appl. No.: 791,133

[22] Filed: Nov. 13, 1991

[30] Foreign Application Priority Data

Nov. 13, 1990 [JP] Japan .................................. 2-306632

[51] Int. Cl.⁵ ............................................. G21K 1/02
[52] U.S. Cl. .................................... 378/148; 378/145; 378/147; 378/160; 378/153
[58] Field of Search ................ 378/145, 147, 148, 149, 378/150, 151, 152, 153, 157, 156, 158, 159, 160; 250/505.1

[56] References Cited

U.S. PATENT DOCUMENTS 4,766,603  8/1988  Okabe et al. ........................ 378/152

FOREIGN PATENT DOCUMENTS

0142841  5/1985  European Pat. Off. .
0166030  1/1986  European Pat. Off. .
3635948  4/1988  Fed. Rep. of Germany .
60-127698  7/1985  Japan .

Primary Examiner—David P. Porta
Assistant Examiner—Don Wong
Attorney, Agent, or Firm—Oblon, Spivak, McClelland, Maier & Neustadt

[57] ABSTRACT

In order to perform stereoradiography, an X-ray apparatus utilizes an X-ray tube having a pair of X-ray focal points. The X-ray beams are alternately irradiated from the focal points toward an image intensifier through a patient and are limited by an X-ray beam limiting device. The device shapes the irradiated X-ray beams onto a circular detection surface of the image intensifier into a polygon such as octagon. The X-ray irradiation field on the detection surface can be circumscribed to a circular input window (i.e. effective input area), preventing the field from going beyond the detection surface. Thus, direct X-ray leaking over the image intensifier is avoidable.

20 Claims, 9 Drawing Sheets

X-RAY APPARATUS

BACKGROUND OF THE INVENTION

The present invention relates to an X-ray apparatus having an X-ray beam limiting device assembled with an X-ray tube for stereoradiography.

In medical examinations such as angiography, stereoradiography has the advantage of being able to obtain stereo images. An X ray apparatus for the stereoradiography has used an X-ray tube having a pair of X-ray focal points positioned a certain distance apart. X-rays are alternately irradiated from the one focal point to the other of the X-ray tube to a living body (a subject) through an X-ray beam limiting device, and the X-ray transmitted through the living body are detected by a film or an image intensifier (referred to as "I.I." hereinafter). An observer can obtain a stereo penetrating image, when his right eye sees an image formed according to the transmitted X-rays from the X-ray focal point and his left eye sees an image formed according to the transmitted X-rays from the X-ray focal point.

Japanese Laid-Open No. 60-127698 discloses a example of X-ray beam limiting devices.

The above-mentioned X-ray beam limiting device is placed at irradiation-opening side of an X-ray tube having a pair X-ray focal points for one target. The X-ray beam limiting device comprises: a rectangular limiting means for rectangularly shaping the X-rays; compensating filters for compensating a difference in the X-ray absorptions by heart muscles and lungs and which are situated at the X-ray-focal-point side of the rectangular limiting means; a circular limiting blade having two circular holes for shaping the X-rays from the X-ray focal points into circles according to a circular effective detection area (i.e. an input window) of an I.I.; and inside limiting blades for shaping the rectangular irradiation field defined by the rectangular limiting means into individual squares for the X-ray focal points.

In normal stereoradiography, a subject contacts the effective detection area. In such contact stereoradiography, the X-ray penetrating image of the subject is detected at an enlargement ratio of 1 to 1, and thus the distance between the X-ray focal points and is 63 mm, which is approximately equal to the distance between the eyes.

The blades of the rectangular limiting means and the inside limiting blades are controlled and moved by a stepping motor so that even when the SID (Source-Image Distance) is changed, a square X-ray irradiation field is circumscribed on the circular effective detection area of the I.I.

Each of the circular holes has a maximum diameter according to the minimum SID. Then, when the SID is at minimum, the X-rays are shaped by the circular holes into a cone, resulting in a circular X-ray irradiation field which coincides with the circular effective detection area, not in a square X-ray irradiation field.

However, when the SID is at maximum or relatively long, a circular X-ray irradiation field on the detection surface resulting from the circular holes would be a circle larger than the exterior of the I.I. As a result, the X-ray is shaped into a pyramid, thus resulting in the square X-ray irradiation field. Four corners of the square X-ray irradiation field may go out of the boundary of the exterior of the I.I.

This results in condition in which some of the X-rays are out of the boundary of the exterior of the I.I. and directly leak behind the I.I. Thus, a patient may receive more X-rays than necessary, or other people like an operator may be exposed to the leaked X-rays.

To the contrary, when the SID setting range is limited to avoid the leakage behind the I.I., the device fails to provide sufficient information for diagnoses due to a short SID.

Presently, there is a demand for a magnifying stereoradiographic device which can both perform high-speed serial stereoradiography (:several frames per second in the case of film photography; several tens of frames per second in the case of I.I. photography) and provide magnified images. For example, for a magnifying stereoradiography with magnification of two in which a subject is placed at the middle between the X-ray focal points and the X-ray detection surface, it is required to use an X-ray tube having an interval between the focal points reduced to approximately 35 mm.

As stated above, where the X-ray tube having shorter distances between the focal points is used, the triangular space, in which the X-ray irradiation is not affected, becomes too small to accomodate the conventional horizontally-moving beam limiting means for preventing the above-mentioned x-ray leakage.

SUMMARY OF THE INVENTION

Thus, it is an object of the present invention to provide an X-ray apparatus having an X-ray beam limiting device which prevents the X-ray beams from directly leaking over the detection surface without restricting the SID or the effective detection area.

It is a further object of the present invention to provide an X-ray beam limiting device which prevents the exterior of the detector from increasing its size.

These and other objects can be achieved according to the present invention, in one aspect by providing, an X-ray apparatus comprising: an X-ray tube having a pair of X-ray focal points placed a predetermined distance apart from each other; an X-ray detector having a detection surface in which an circular input window is placed; and a X-ray beam limiting device for limiting an X-ray beam irradiated from each of the X-ray focal points of the X-ray tube onto the circular input window of the X-ray detector, wherein the beam limiting device includes an element for limiting the X-ray beams so that an irradiation field of each one of the X-ray beams onto the detection surface can be formed into shape which is circumscribed on the circular input window.

Preferably, the limiting element comprises a blade unit consisting of a plurality of blades and being capable of limiting each of the X-ray beams to the polygonal shape which enables the X-ray irradiation field onto the detection surface of the X-ray detector to be circumscribed on the input window and to remain within the detection surface, and a control unit for adjusting each position of the plural blades.

The X-ray detector is preferably an image intensifier and the polygonal shape is preferably approximately octagonal.

It is preferred that the blade unit comprises a first set of blades projecting a V-shaped aperture having a base to the detection surface, a second set of blades projecting a V-shaped aperture to the detection surface, and a third set of blades projecting a rectangular aperture to the detection surface. Further, the first set of blades and the second set of blades are placed so that the V-shaped aperture having the base projected by one of the first set of blades and the V-shaped aperture projected by one of the second set of blades are faced each other in a longitudinal direction of the rectangular aperture projected by the third set of blades. The three sets of blades are placed, from one side near to the X-ray tube toward another side near to the X-ray detector, in an order of positioning from the first to the third set of blades.

It is preferred that the first set of blades are individually rotatable round an axis right to a longitudinal direction of the rectangular aperture. Also, it is preferred that the second set of blades are slidable in a transverse direction right to a longitudinal direction of the rectangular aperture, and the third set of blades are slidable in transverse and longitudinal directions of the rectangular aperture.

Further, it is preferred that the control unit is able to adjust each position of the blades in accordance with at least either one of a distance between the X-ray tube and the X-ray detector, and a size of the input window of the X-ray detector.

As a result, the irradiation field of the X-ray beams onto the detection surface of the detector can be formed by the first to third set of blades into an almost octagonal shape, which is circumscribed on the input window. And more, when the distance between the X-ray tube and the X-ray detector is changed, it can be kept that the irradiation field is circumscribed on the input window. Thus, the irradiation field can be rounded along the boundary of the input window as possible as it could be, and remains within the detection surface. This prevents x-ray beams from leaking over the X-ray detector.

BRIEF DESCRIPTION OF THE DRAWINGS

The accompanying drawings which are incorporated in and constitute a part of this specification, illustrate embodiments of the present invention and, together with the description, serve to explain the principles of the present invention; in which.

DESCRIPTION OF THE PREFERRED EMBODIMENTS

An embodiment of an X-ray apparatus in accordance with the present invention will now be described with reference to FIG. 1 to FIG. 13.

Figure 1:
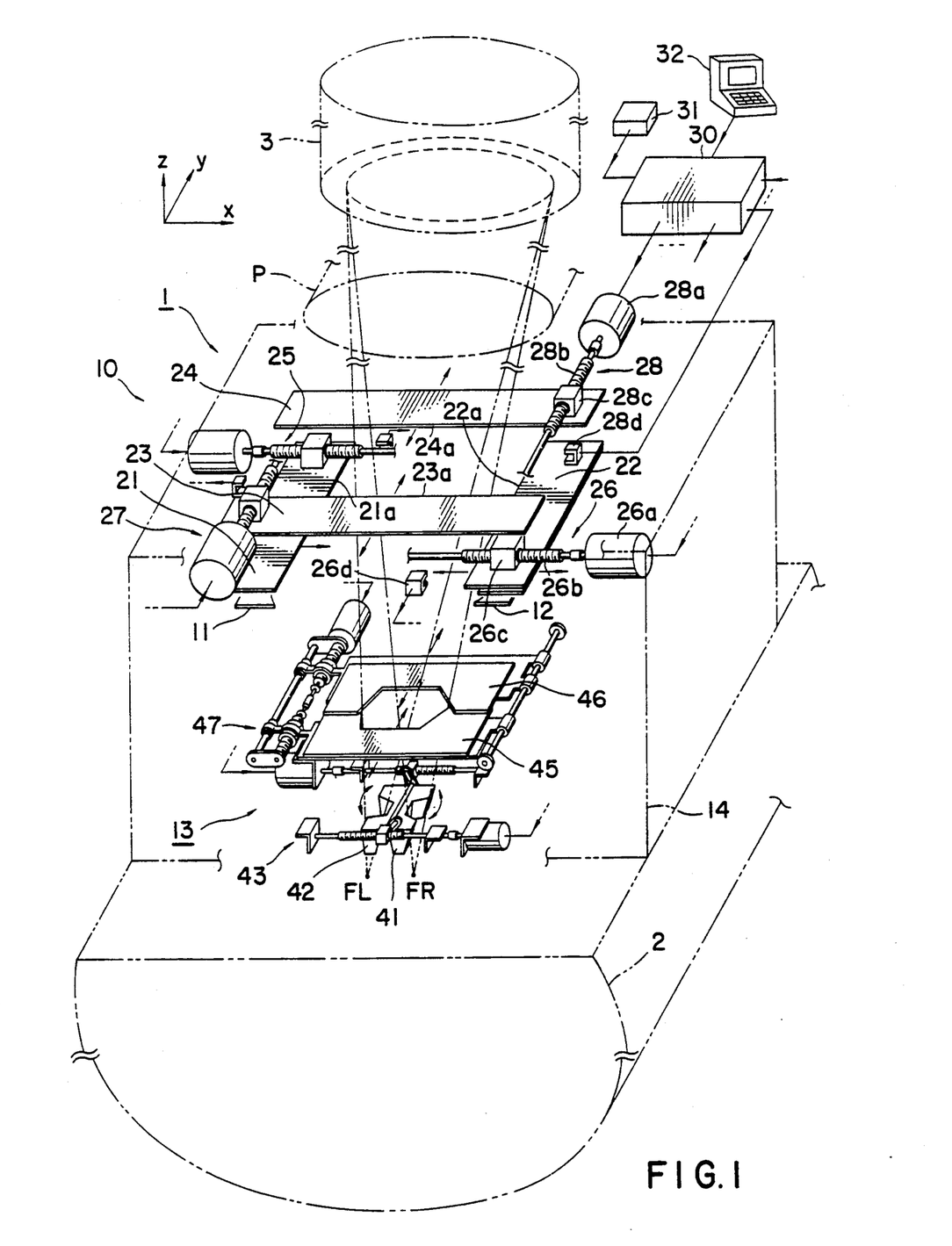
FIG. 1 is a perspective view showing an essential portion of an X-ray beam limiting device according to a preferred embodiment of the present invention.

FIG. 1 is a perspective view of an essential portion of an X-ray apparatus having an X-ray beam limiting device 1. The device 1 is assembled with an X-ray tube 2 having a pair of X-ray focal points FR, FL whose interval is 35 mm. An I.I. (Image Intensifier) 3 is placed, apart from the X-ray beam limiting device 1, at a position which faces the device 1. In the FIG. 1, a reference alphabet P represents a patient to be examined.

The I.I. 3 has a detection surface S formed in one side of an cylindrical exterior 3a. The detection surface S includes an input window Se as an effective detection area for X-ray beams. The remaining area excepting the input window Se on the detection surface S forms a torus-like surface, as shown in FIGS. 1 and 9 to 13 and is lead made for absorbing X-ray beams.

The X-ray beam limiting device 1 comprises a rectangular limiting mechanism 10, compensating filters 11, 12 and a polygonal limiting mechanism 13. Those limiting mechanism 10, 13 and filters 11, 12 are assembled inside a box-like casing 14.

The rectangular limiting mechanism 10 has right and left-side limiting blades 21, 22 for limiting X-ray beams in the x-direction, back and forth-side limiting blades 23, 24 for limiting X-ray beams in the y-direction, driving mechanisms 25, 26 for driving the right and left-side blades 21, 22 respectively, and driving mechanisms 27, 28 for driving the back and forth-side limiting blades 23, 24 respectively. For the blade 22 only, a double-plate structure is adopted to gain a wide moving distance in x-direction.

All the blades 21 to 24 are shaped into rectangular plates and made of lead. The right and left-side limiting blades 21, 22, having straight-line edges 21a, 22a for limiting X-ray beams respectively, are placed in parallel at a certain level. The back and forth-side limiting blades 23, 24, also having straight-line edges 23a, 24a for limiting X-ray beams respectively are placed in parallel at a certain horizontal level nearer to the X-ray tube 2, on condition that the blades 23, 24 and 21, 22 cross at a right angle each other.

Each of the above-mentioned driving mechanisms 25 to 28 includes a stepping motor 25a (to 28a), a lead screw 25b (to 28b) attached on the output shaft of the stepping motor 25a (to 28a), a nut 25c (to 28c) engaged with the lead screw 25b (to 28b) and fixed to the blade 25 (to 28), and a photo sensor 25d (to 28d). The output shafts of the motor 25a to 28a are rotatably supported at their both ends on the casing 14. The stepping motors 25a to 28a are driven individually by driving signals supplied from a controller 30. The controller 30 receives sensing signals detected by the photo sensors 25d to 28d to control initial positions of the blades 21 to 24. Then, rotation of the stepping motors 25a to 28a enables the blades 21 to 24 to move in either way of the predetermined x and y-axis directions.

In this X-ray apparatus, an SID sensor 31, which is formed using a potentiometer, is provided for sensing a distance between the X-ray tube 2 and the I.I. 3. Also, there provided is an input and display unit 32 for operation.

The above-mentioned compensating filters 11, 12 are placed in parallel between the rectangular limiting mechanism 10 and the polygonal limiting mechanism 13. And, the filters 11, 12, made of lead, have a heart-shape edges at their face-to-face sides to cut excessive X-rays. The filters 11, 12 can be also slid in predetermined axis directions using stepping motors (not shown in FIG. 1) under control of the controller 30.

The above-mentioned polygonal limiting mechanism 13 is placed at the nearest position to the X-ray tube 2, as shown in FIG. 1. The mechanism 13 comprises: inside rotatable blades 41, 42 for limiting an X-ray irradiation field from the inside thereof; inside-rotatable-blade driving mechanism 43 for driving the inside rotatable blades 41, 42; outside blades 45, 46 for limiting the X-ray irradiation field from the outside thereof; and outside-blade driving mechanism 47 for driving the outside blades 45, 46.

Figure 2:
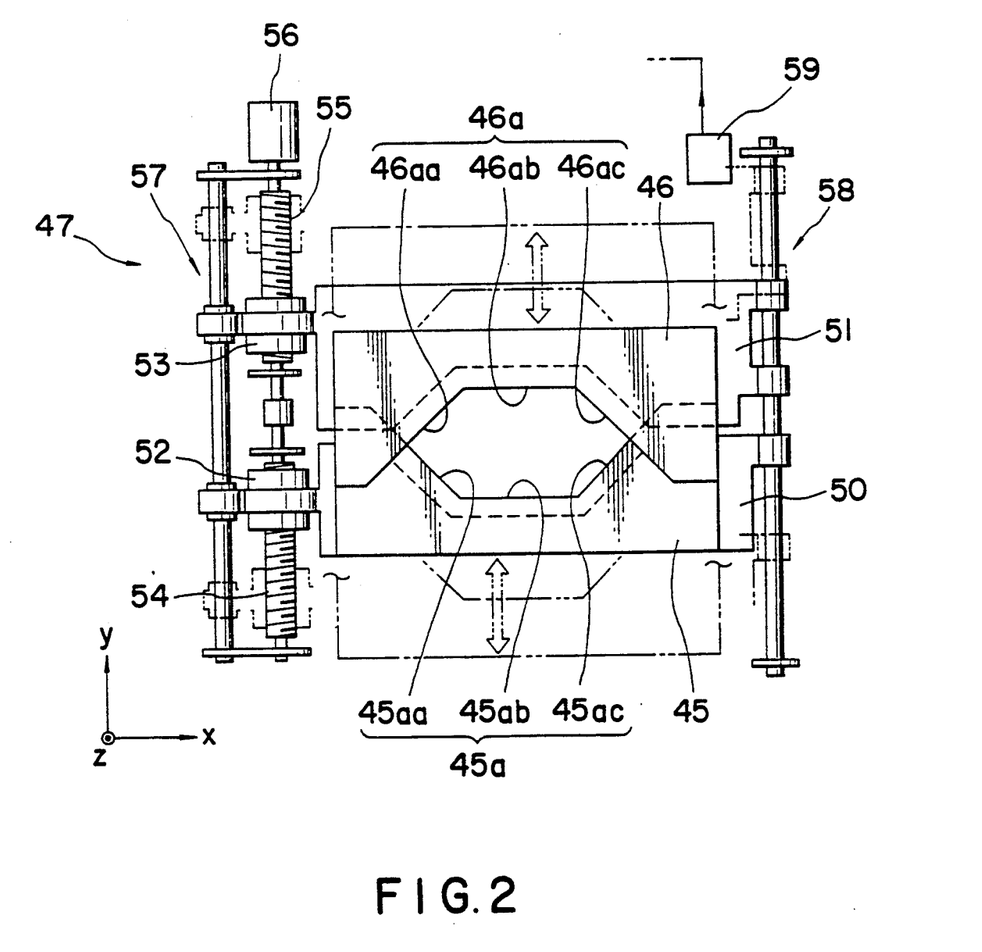
FIG. 2 is a plan view of outside blades and their driving mechanism shown in FIG. 1.

The outside blades 45, 46, made of lead, are each shaped into a thin rectangular plate having a cut 45a (46a) which is open to its one edge, as shown in FIG. 2. Each cut 45a (46a) is made up of two oblique segments 45aa, 45ac (46aa, 46ac) which are cutted in obliquely from the edge, and a parallel segment 45ab (46ab) as a bottom which is parallel to the edge and connected the two oblique segments 45aa, 45ac(46aa, 46ac). The outside blades 45, 46, by the outside-blade driving mechanism 47, are placed in parallel and on condition that the cut 45a, 46a are face-to-face, but are at different levels, enabling them to overlap each other.

The outside-blade driving mechanism 47 includes, as shown in FIG. 2: mounting plates 50, 51 mounting the outside blades 45, 46; nuts 52, 53 each connected to one end of each of the mounting plates 50, 51; a right-handed leading screw 54 screwed through the nut 52; a left-handed leading screw 55 screwed through the nut 53 and integrally connected to the screw 54; a stepping motor 56 for rotating the lead screw 55; and slide bearing mechanisms 57, 58 by which the outside blades 45, 46 smoothly can move translationally in the y direction opposite to each other. The mechanism 47 is also provided with a photo sensor 59 for initialization of the blade positions. For example, when the leading screws 54, 55 are rotated in one direction by the motor 56, the outside blades 45, 46 move away from each other (refer to two-dotted lines), and when the leading screws 54, 55 are rotated in the other direction, the outside blades 45, 46 move closer to each other.

The inside rotatable blades 41, 42 are placed in a triangular space formed by inside boundaries XR1a, XR2a of the x-ray beams XR1, XR2 irradiating from the X-ray focal points FR, FL and a line LN between the focal points FR, FL. The driving mechanism 43 for the blades 41, 42 is symmetrically designed or positioned in FIGS. 3 to 5.

Figure 3:
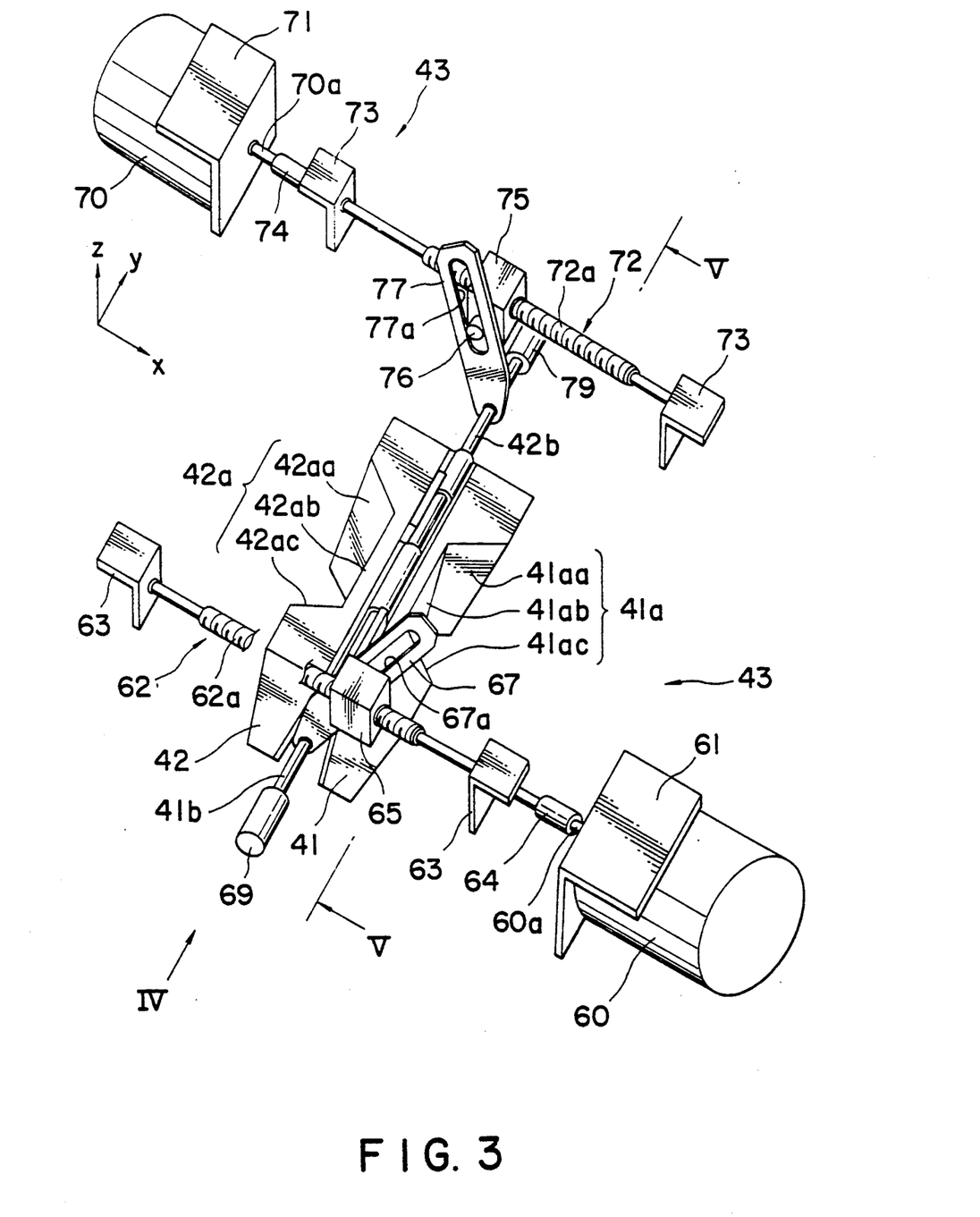
FIG. 3 is a perspective view of inside rotatable blades and their driving mechanism shown in FIG. 1.

As shown in FIG. 3, each of the blades 41 and 42 has a recess 41a (42a) large enough to cover X-ray XR1 (XR2) irradiating from the focal points FR, FL with a spreading angle θ (refer to FIG. 5) in the y-direction along the side of the device I; and the rotatable shaft 41b (42b) fixed at a first end to the recess 41a (42a). Each one of the recesses 41a, 42a is formed by cutting from one side, or has two oblique-cutted surfaces 41aa, 41ac (42aa, 42ac) cutted obliquely from the side and parallel-cutted surface 41ab (42ab) as a bottom parallel to the side. As shown in FIGS. 6A, 6B, shapes of the recesses 41a, 42a are designed to be a pyramid according to the shape of X-ray beams at the maximum aperture. The inside rotatable blades 41, 42 are also made of lead.

Figure 4:
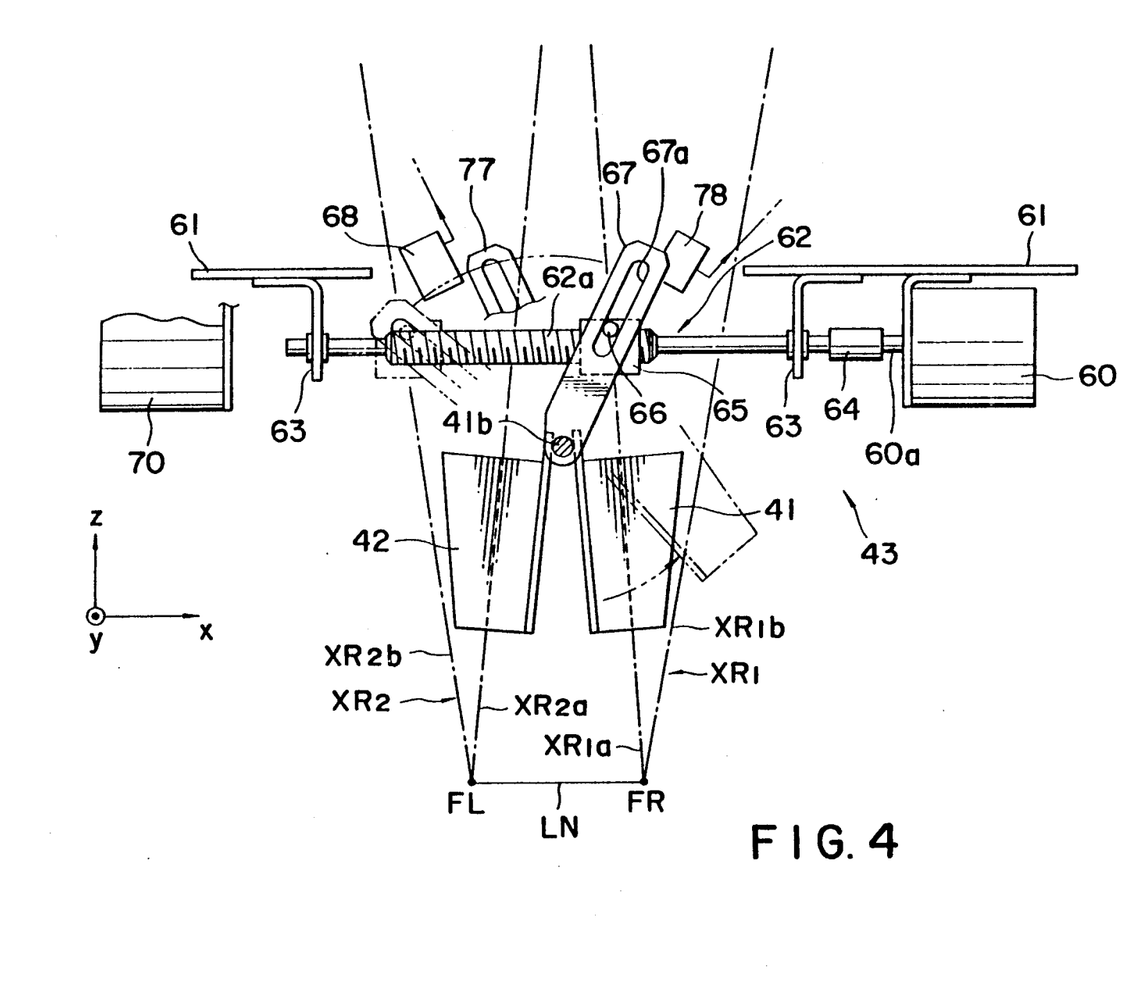
FIG. 4 is a side view of the inside rotatable blades and their driving mechanism shown in FIG. 3, when seen along a y-direction.

For one inside rotatable blade 41, as shown in FIGS. 3 and 4, the inside-rotatable-blade driving mechanism 43 includes: a stepping motor 60 which is a drive source for the rotation of blade 41 and is fixed to a base 61; a leading screw shaft 62 rotatably connected at both ends thereof by L-shaped metal fixtures 63, 63 to the base 61 and coupled by a coupling 64 to an output shaft 60a of the motor 60; a nut 65 having a pin 66 and screwed onto a leading screw portion 62a of the shaft 62; and a guide plate 67 which has a long hole 67a associated with the pin 66 and is rotatable centered at the rotatable shaft 41b. The blade 41 is fixed to an end portion of the guide plate 67 so as to rotate centered at the rotatable shaft 41b as the guide plate 67 rotates. The mechanism 43 is provided with a photo sensor 68 to initialize the position of the blade 41 (refer to FIG. 4).

For the other inside rotatable blade 42, the mechanism 43 also includes, on the same principle as the blade 41, a stepping motor 70 fixed to a base 71, a leading screw shaft 72 supported rotatably by L-shaped metal fixtures 73, 73 and coupled by a coupling 74 to the motor shaft 70a, a nut 75 having a pin 76 and screwed onto a leading screw portion 72a of the shaft 72, and a guide plate 77 having a long hole 77a associated with the pin 76 and is fixed to the rotatable shaft 42b. The blade 42 is fixed to an end portion of the guide plate 77 so as to rotate centered at the rotatable shaft 42b as the guide plate 77 rotates. The mechanism 43 is also provided with a photo sensor 78 to initialize the position of the blade 42 (refer to FIG. 4).

The rotatable shaft 41b of the blade is placed so that the center line thereof coincides with the center line of the other rotatable shaft 42b of the inside rotatable blade 42, and thus the driving mechanism 43 for the inside rotatable blades 41, 42 is made compact. The rotatable shaft 41b, 42b, at a middle portion thereof, are fitted and fixed to the guide plate 67, 77 respectively, and, at the second end, are supported by a ball bearing 69, 79 respectively so as to rotate smoothly.

The inside rotatable blade 41 adjusts the radiating X-ray XR1 from the inside boundary XR1a. The inside rotatable blade 42 restricts the pyramid-shaped X-ray XR2 from the inside boundary XR2a (refer to FIG. 8).

When the stepping motor 60 rotates, the nut 65 moves along the leading screw portion 62a to a position shown by a two-dot line in FIG. 4; the guide plate 67 rotates on the rotatable shaft 41b to a position shown by a two-dot line; and the blade 41 rotates to a position shown by a two-dot line. The other inside rotatable blade 42 is also rotated to a position in the opposite direction by the other stepping motor 70, thus being able to take a position symmetric to that of the blade 41.

Various signals, including the sensing signals from the photo sensors 25d~28d, 59, 68, 78, radiography-selection signals (i.e. stereoradiography or monoscopicradiography), and SID signals from the SID sensor 31, are supplied to the controller 30. The controller 30 is provided with a computer to process the input signals according to predetermined procedures shown in FIG. 7 and to calculate driving signals for the stepping motors 25a~28a, 56, 60, 70. The procedure for X-ray limiting control is designed so that when the SID is changed, the irradiation fields from the two X-ray focal points FL, FR can meet exactly a circular input window Se in the circular detection surface S of the X-ray tube 2.

The operation of the X-ray beam limiting device 1 according to this embodiment as described above will be explained with reference to FIGS. 7 to 12 (FIGS. 8 to 12 show plan views of a concerned portion of the device, illustrating the X-ray irradiation fields projected on the detection surface S).

First, the operation of the controller 30 will now be explained with reference to FIG. 7.

Figure 7:
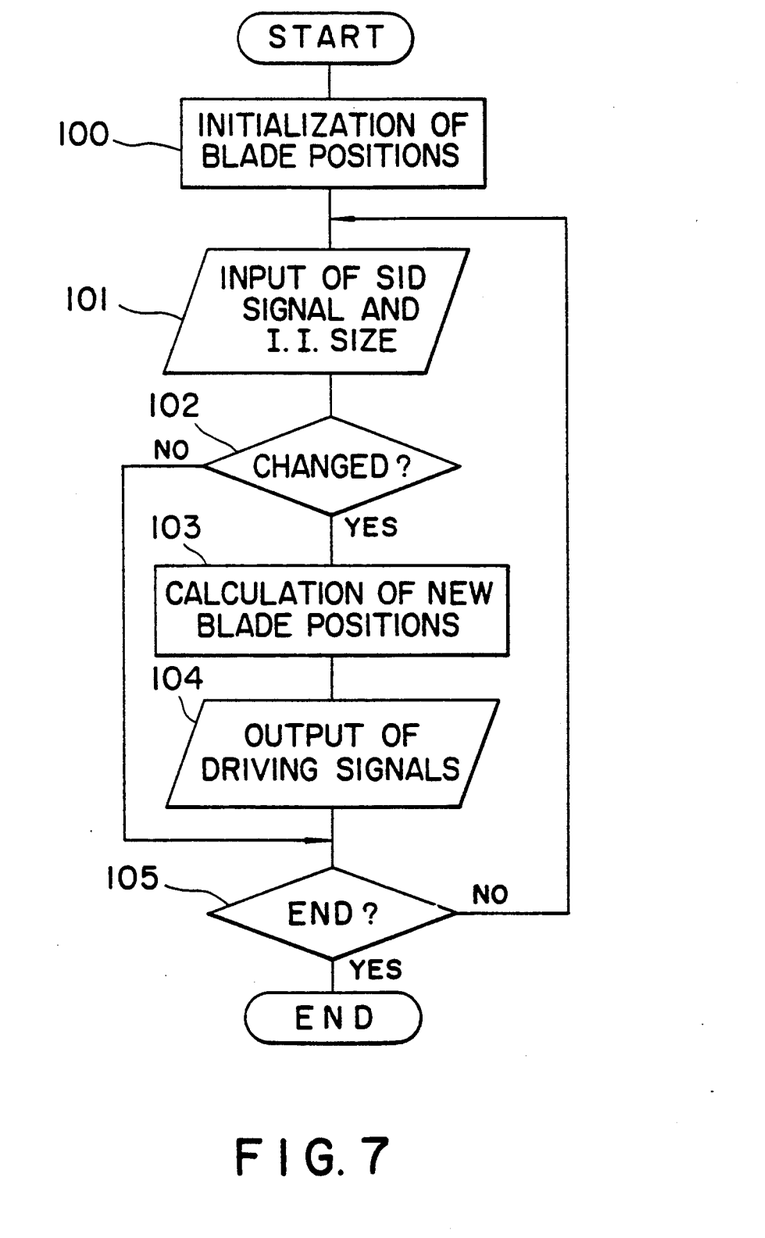
FIG. 7 is a flowchart showing processing in a controller shown in FIG. 1.

After initiated, at the first Step 100 of the flowchart in FIG. 7, the controller 30 will order initialization of each position of all the blades 11 to 14, 41, 42, 45 and 46 using the sensing signals from the photo sensors 25d to 28d, 59, 68 and 78. The controller 30 drives the stepping motors 25a to 28a, 56, 60 and 70 until sensing light beams will be cut by the blades 11 to 14, 41, 42, 45 and 46 or their related portions. Then, the cutted light beams allow the controller 30 to move all the blades 11 to 14, 41, 42, 45 and 46 individually to their predetermined initial positions by driving the stepping motors 25a to 28a, 56, 60 and 70.

Then, at Step 101, the SID sensing signal from the SID sensor 31 and size information of I.I. 3 will be read in by the controller 30, then, proceeding to Step 102. At the Step 102, the SID sensing signal and I.I. size information are judged whether their values are changed against their previous ones or not. As judgement "YES" (i.e. changed) is made in Step 102, a process of Step 103 will be followed.

At Step 103, each new position and moved direction of all the blades 11 to 14, 41, 42, 45 and 46 according to the newly designated SID or I.I. size is calculated by the controller 30. After this, at Step 104, the controller 30 will supply driving signals corresponding to the calculated values to the stepping motors 25a to 28a, 56, 60 and 70.

Finally, at Step 105, it is judged that the termination of the X-ray limitation control is ordered or not by an operator. If judgement "NO" (i.e. nontermination) is made at Step 105, the processing will be returned to Step 101.

In case judgement "NO" (i.e. unchanged) in Step 102, the processing will be directly jumped to Step 105.

Next, the operation of whole system will be explained, mainly, with focusing on the limitation control of the X-ray beam XR2 from the left-side X-ray focal point FL.

When an operator selects stereoradiography and determines SID, the controller 30 will be initiated to supply driving signals individually to the stepping motors 25a to 28a, 56, 60 and 70 of the mechanisms 10 and 13.

Figure 8:
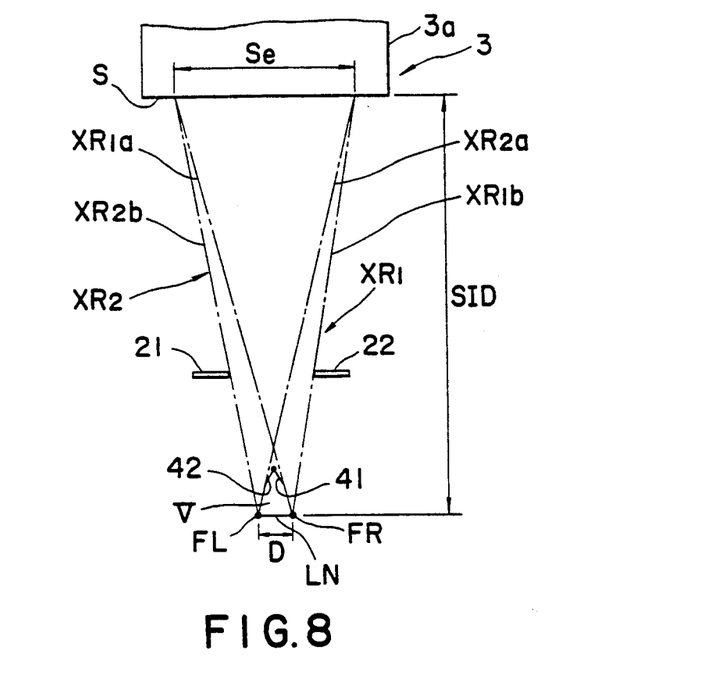
FIG. 8 illustrates operation of a combination of the inside rotatable blades and right and left-side limiting blades shown in FIG. 1.
Figure 9:
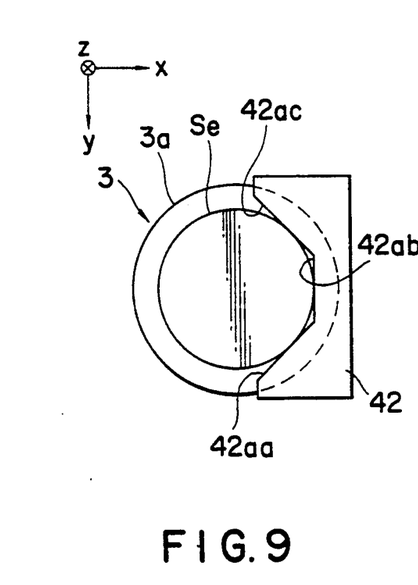
FIG. 9 illustrates an aperture projected onto a detection surface by one of the inside rotatable blades.

In the inside-rotatable-blade driving mechanism 43, under the control of the controller 30, the stepping motor 60, 70 rotates the inside rotatable blades 41, 42 near the centers of the irradating X-ray beams XR1, XR2, as shown in FIG. 8. These blades 41, 42 form the inside boundaries of the irradiation fields respectivly. Then, the spreading angles of the pyramid-shaped X-ray beams XR1, XR2 from the X-ray focal points FR, FL correspond to an input window (effective detection area) Se shared by the X-ray beams XR1 and XR2 on a detection surface S. That is, projected aperture edges 42aa to 42ac of the inside rotatable blade 42 are circumscribed on the input window (effective detection area) Se of the I.I. 3 as shown in FIG. 9.

Figure 10:
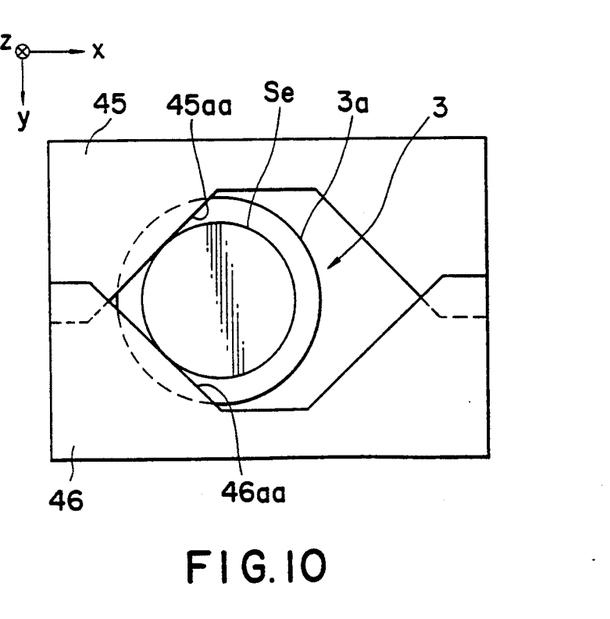
FIG. 10 shows an aperture projected onto the detection surface by of the outside blades.

The stepping motor 56 of the outside-blade driving mechanism 47 shown in FIG. 2 moves the outside blades 45, 46 under the control of the controller 30, so that projected aperture edges 45aa, 46aa of the outside blades 45, 46 are circumscribed on the input window Se of the I.I. 3 as shown in FIG. 10.

Figure 5:
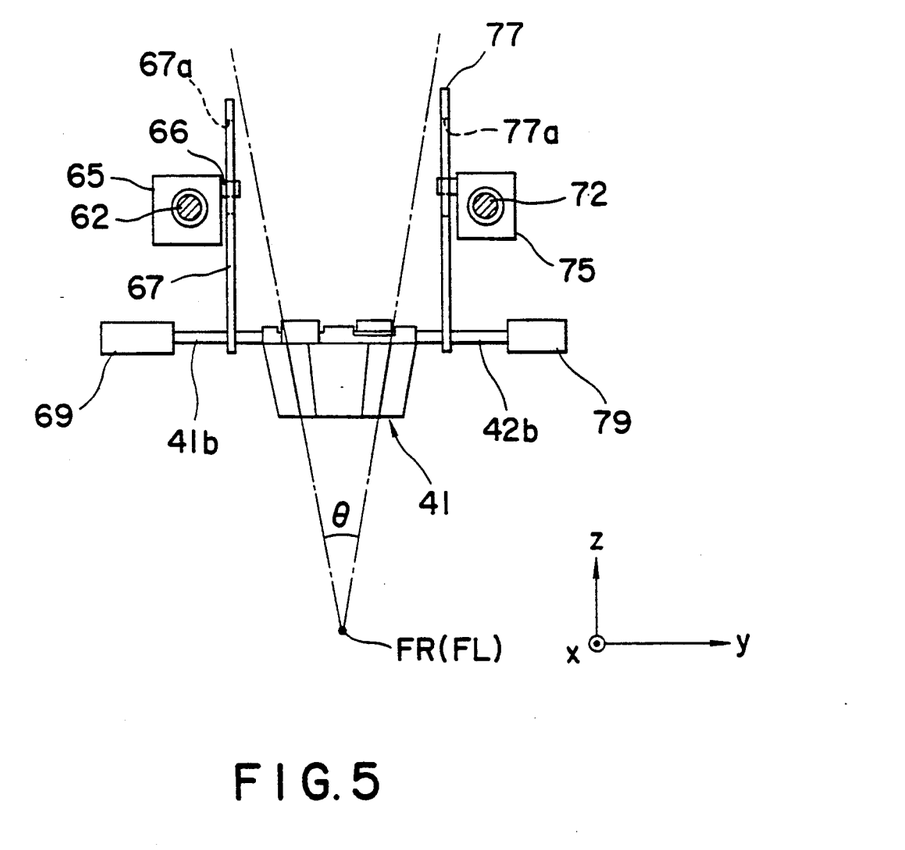
FIG. 5 is a side view of the inside rotatable blades and their driving mechanism shown in FIG. 3, when seen along an x-direction.
Figure 6A:
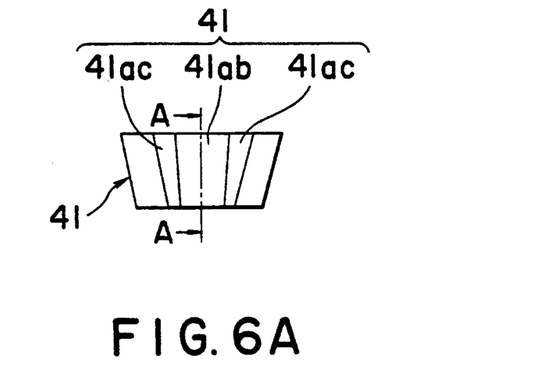
FIG. 6A is a front view of one of an inside rotatable blade.
Figure 6B:
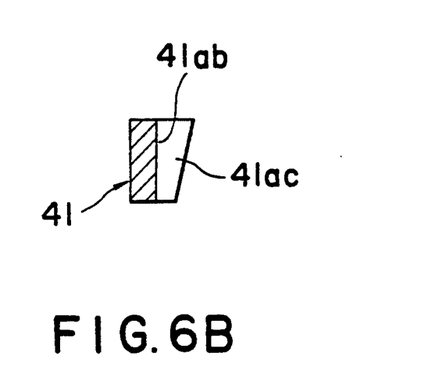
FIG. 6B is a cross-sectional view of the inside rotatable blade shown in FIG. 6A, taken along a line A—A.
Figure 11:
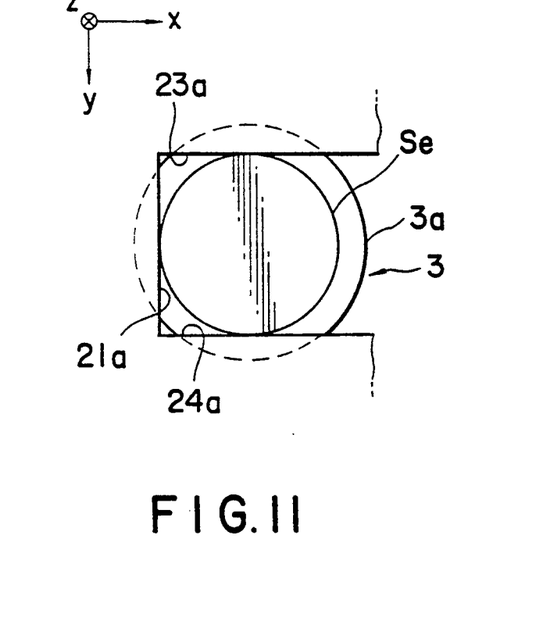
FIG. 11 shows an aperture projected onto the detection surface by the left-side and back and forth-side limiting blades.

The stepping motor 25a to 28a of the rectangular limiting mechanism 10 rotates the blades 11 to 14, under the control of the controller 30, so that projected aperture edges 21a, 23a, 24a of the blades 21, 23, 24 are circumscribed on the input window Se of the I.I. 3 as shown in FIGS. 5 and 11.

Figure 12:
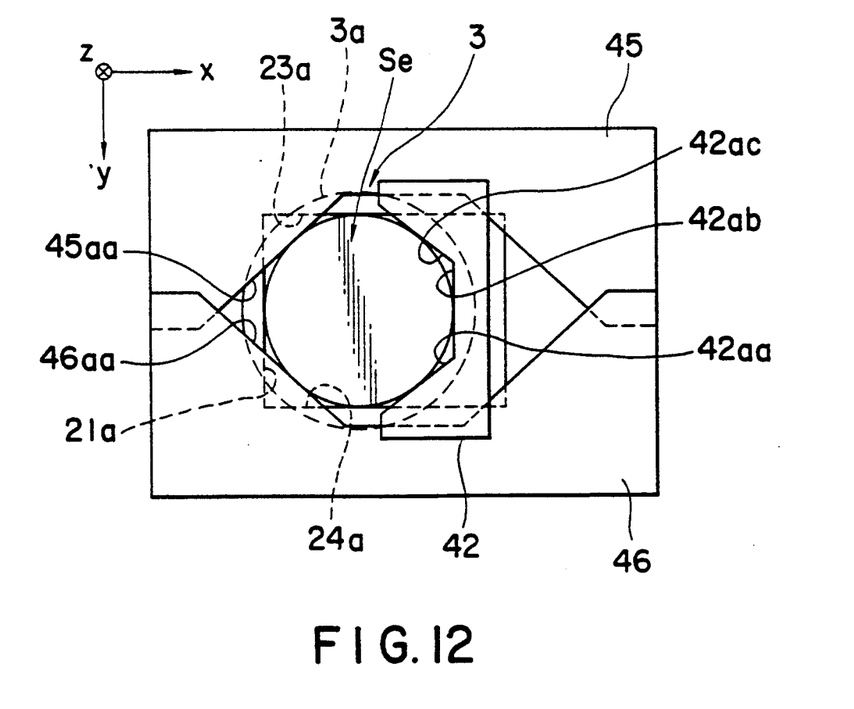
FIG. 12 shows an combined aperture of all the blades gathered to make an octagon for a left-side X-ray focal point.

Thus, by the combined operations of the mechanisms 10 and 13, the X-ray beam XR2 from the left-side X-ray focal point FL is limited to form a substantial half regular octagon which is surrounded by the projected aperture edges 21a, 45aa, 23a, 42ac, 42ab, 42aa, 24a and 46aa and circumscribed on the input window Se of the I.I. 3. That is, the irradiation field is rounded along the circular boundary of the input window Se, and remains within the detection surface s. Therefore, the X-ray XR2 will not directly leak behind an exterior 3a of the I.I. 3.

In the same way, the X-ray beam XR1 from the right-side X-ray focal point XR is limited by the operation of the mechanisms 10 and 13, and thus the X-ray beams XR1 and XR2 will not directly leak behind the exterior 3a of the I.I. 3.

Figure 13:
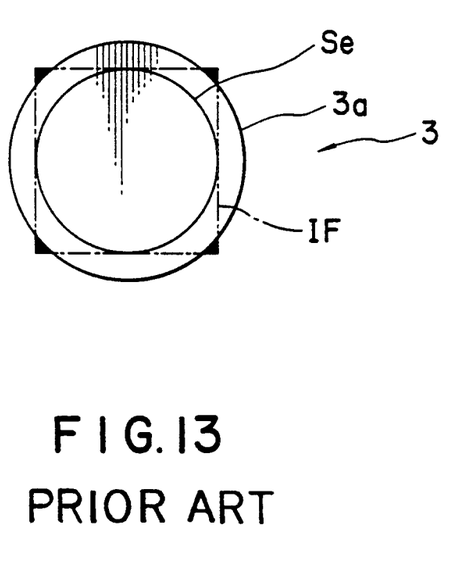
FIG. 13 represents a rectangular aperture according to a conventional X-ray beam limiting device.

If the prior art is adopted, a rectangular aperture IF according to the prior art may be represented as shown in FIG. 13. The four corners (refer to portions painted black) of the rectangular aperture IF in FIG. 13 go out of the boundary of the exterior 3a of the detector 3. Those four corners cause X-ray leaking.

To the contrary, the device 1 according to this embodiment can keep the irradiation field within the detection surface s, and prevent the X-ray beams from directly leaking behind the detection surface s without restricting the SID or the size of the input window.

Even if an X-ray tube having an interval of the X-ray focal points as close as 35 mm is employed, the device still can perform magnifying stereoradiography without restricting the SID or the input window.

The present invention is not restricted by the above embodiment but can be changed or modified within the scope of the invention. For example, the shape of irradiation field on the detection surface S is not restricted to be octagonal, but polygonal shapes having angles more than the octagon may be adopted. By the way, the above-mentioned X-ray beam limiting device 1 is described for use in stereoradiography, but usable as a device for monoscopicradiography.

What we claim is:

1. An X-ray apparatus used in stereoradiography of an object, comprising:

an X-ray tub having a pair of X-ray focal points placed a predetermined distance apart from each other in a first direction, the pair of X-ray focal points emitting a pair of irradiating X-ray beams toward the object along a second direction approximately perpendicular to the first direction;

an X-ray detector having a circular input window and a detection surface for receiving X-ray beams transmitted from the X-ray tube and irradiated through the object; and an X-ray beam limiting device, arranged between said X-ray tube and said object, for limiting irradiation fields of the X-ray beams, including;

a first set of blades made of an X-ray shielding material including two first blades, each blade having a front with a notch therethrough for allowing X-ray beams from said X-ray tube to pass therethrough, and each blade having a back opposed to the front of the blade, the two first blades being arranged back to back along a third direction approximately perpendicular to the first and second directions in a space between the pair of X-ray beams;

a first driving unit for supporting the two first blades pivotally around an axis parallel to the third direction and for pivoting said first blades in response to a control signal;

a second set of blades made of X-ray shielding plates which are substantially impenetrable to X-rays and include two second blades, each second blade having a notch therethrough for allowing said irradiating X-ray beams to pass therethrough, the two second blades arranged between said first set of blades and said object and arranged such that the notches of the second blades face each other;

a second driving unit for supporting the two second blades slidably in a direction parallel to the third direction and for moving said second blades in response to said control signal;

a third set of blades made of X-ray shielding plates and including a plurality of third blades arranged to form an adjustable rectangular aperture approximately perpendicular to said irradiating X-ray beams, said third set of blades located between said second set of blades and said object;

a third driving unit for supporting said third set of blades and for moving the plurality of third blades to adjust the rectangular aperture in response to said control signal;

means for controlling the first, second, and third driving units by supplying the control signal in accordance with at least one of a distance between said X-ray tube and said X-ray detector, and a size of the input window of the X-ray detector.

2. An apparatus as claimed in claim 1, further comprising:

filters for cutting excessive X-rays of the X-ray beams, the filters being disposed between the second set of blades and the third set of blades.

3. An apparatus as claimed in claim 1, wherein said X-ray detector is an image intensifier.

4. An apparatus as claimed in claim 3, wherein said detection surface of the image intensifier has a torus-like surface around the circular input window, the torus-like surface being made of X-ray shielding material.

5. An apparatus as claimed in claim 4, wherein said second blades are disposed in different planes, each plane being approximately parallel to both the first and the third directions.

6. An apparatus as claimed in claim 4, wherein said third set of blades consist of four third blades defining said adjustable rectangular aperture.

7. An apparatus as claimed in claim 4, wherein said control means supplies the control signal to said driving units so that said X-ray limiting device forms an irradiation field of the X-ray beams onto the detection surface into a shape approximately circumscribed on the circular input window.

8. An apparatus as claimed in claim 7, wherein said shape lies within the torus-like surface.

9. An apparatus as claimed in claim 8, wherein said shape is a polygon having more than four sides.

10. An apparatus as claimed in claim 9, wherein said polygonal is an octagon.

11. An apparatus as claimed in claim 4, wherein said notches of said first set of blades are formed such that a portion of each notch located toward said X-ray tube is smaller than a portion of each notch located away from said X-ray tube and thereby said notches are gradually increasing in size in the second direction from an end nearer to the X-ray tube to an opposite end nearer to the second set of blades.

12. An apparatus as claimed in claim 11, wherein a spreading angle of said X-rays emitted from said X-ray tube is approximately equal to an angle formed in said notches of said first set of blades by said increase in size of said notches.

13. An apparatus as claimed in claim 11, wherein each first blade has a different pivot axis parallel to the third direction.

14. An apparatus as claimed in claim 13, wherein said different pivot axes of said first blades are disposed at the backs of the respective first blades and located on a portion of the respective first blades closer to the second set of blades than a portion of the respective first blades closer to the X-ray tube.

15. An apparatus as claimed in claim 14, wherein said first driving unit has two electric motors to receive the control signal, two transmission mechanisms each transmitting drive forces generated by the two motors and two pivot mechanisms, thereby pivoting the two first blades about the respective axes with the drive forces transmitted by the two transmission mechanisms.

16. An apparatus as claimed in claim 15, wherein said motors are electrical stepping motors.

17. An apparatus as claimed in claim 16, wherein said first driving unit pivots the two first blades in opposite pivoting directions.

18. An apparatus as claimed in claim 17, wherein said second set of blades are slidable in in opposite directions parallel to the third direction.

19. An apparatus as claimed in claim 18, wherein said second driving unit has a single electric motor to receive the control signal and a transmission mechanism for transmitting a drive force generated by the motor to the two second blades.

20. An apparatus as claimed in claim 19, wherein the third set of blades form two pairs, one pair forming edges of the adjustable rectangle parallel to the first direction and being slidable in the third direction and the other pair forming edges of the adjustable rectangle parallel to the third direction and slidable in the first direction.

* * * * *